US010816532B2

(12) United States Patent
Zhu et al.

(10) Patent No.: US 10,816,532 B2
(45) Date of Patent: Oct. 27, 2020

(54) METHODS AND DEVICES FOR DETECTING MERCURY ISOTOPES IN CRUDE OIL

(71) Applicant: PetroChina Company Limited, Beijing (CN)

(72) Inventors: Guangyou Zhu, Beijing (CN); Shunlin Tang, Beijing (CN)

(73) Assignee: PetroChina Company Limited, Beijing (CN)

( * ) Notice: Subject to any disclaimer, the term of this patent is extended or adjusted under 35 U.S.C. 154(b) by 0 days.

(21) Appl. No.: 16/389,481

(22) Filed: Apr. 19, 2019

(65) Prior Publication Data
US 2020/0132659 A1 Apr. 30, 2020

(30) Foreign Application Priority Data
Oct. 31, 2018 (CN) .......................... 2018 1 1284132

(51) Int. Cl.
*G01N 21/31* (2006.01)
*H01J 49/00* (2006.01)
(Continued)

(52) U.S. Cl.
CPC ..... *G01N 33/2835* (2013.01); *G01N 21/3103* (2013.01); *H01J 49/105* (2013.01); *G01N 2021/3107* (2013.01)

(58) Field of Classification Search
CPC .. B01D 53/64; B01D 2257/602; B01D 53/75; B01D 53/8665; G01N 21/3103; G01N 31/005; G01N 33/2858
(Continued)

(56) References Cited

U.S. PATENT DOCUMENTS 4,758,519 A * 7/1988 Nakao ................ G01N 21/3103
422/83
6,197,269 B1 * 3/2001 Jansen .................... B01D 53/64
423/243.01
(Continued)

FOREIGN PATENT DOCUMENTS

CN 201740738 U 2/2011
CN 102608271 A 7/2012
(Continued)

OTHER PUBLICATIONS

English-language Abstract of Chen, Gengliang, "Standardization of Mercury Determination in Natural Gas," Petroleum Planning & Engineering, vol. 8, No. 1, 4 pages (Jan. 1997).
(Continued)

*Primary Examiner* — David A Vanore
(74) *Attorney, Agent, or Firm* — Foley & Lardner LLP

(57) ABSTRACT

The present disclosure relates to a method and device for detecting mercury isotopes in crude oil. The device comprises an enrichment-absorption system and a secondary purification-enrichment system for mercury isotopes, wherein the enrichment-absorption system includes an air-background mercury absorption system, a pyrolysis/cracking system, a mercury-sample absorption system connected in series with pipe lines, and a vacuum pump, and the vacuum pump is connected to the mercury-sample absorption system through a pipe line; the secondary purification-enrichment system includes a nitrogen-gas cylinder, a collection bottle with potassium permanganate absorption liquid, and a secondary enrichment-absorption bottle connected in series with pipe lines, wherein the secondary purification-enrichment system further includes a stannous-chloride storage bottle, which is connected to a pipe line between the nitrogen-gas cylinder and the collection bottle (Continued)

with potassium-permanganate absorption liquid via a peristaltic pump and through a pipe line.

19 Claims, 2 Drawing Sheets

(51) Int. Cl.
*B01D 53/64* (2006.01)
*G01N 33/28* (2006.01)
*H01J 49/10* (2006.01)

(58) Field of Classification Search
USPC ........ 250/281, 282, 288; 422/129, 169, 172, 422/198, 255, 83; 73/53.07
See application file for complete search history.

(56) References Cited

U.S. PATENT DOCUMENTS

| | | | |
|---|---|---|---|
| 9,125,596 B2* | 9/2015 | Leclerc | A61B 5/1172 |
| 9,712,035 B1* | 7/2017 | Bango | F04B 35/04 |
| 9,988,584 B2* | 6/2018 | Oehr | C10G 1/00 |
| 2002/0033097 A1* | 3/2002 | El-Shoubary | B01J 20/0237 |
| | | | 95/134 |
| 2006/0021506 A1* | 2/2006 | Hakka | B01D 53/507 |
| | | | 95/129 |
| 2009/0004644 A1* | 1/2009 | Kiel | C12N 15/115 |
| | | | 435/5 |
| 2009/0169450 A1* | 7/2009 | Naito | B01D 53/75 |
| | | | 423/210 |
| 2010/0126909 A1* | 5/2010 | Bhasin | B01J 20/3236 |
| | | | 208/135 |
| 2012/0067786 A1* | 3/2012 | Gallup | C10G 27/02 |
| | | | 208/252 |
| 2012/0205533 A1* | 8/2012 | Ariya | G01N 1/405 |
| | | | 250/282 |
| 2013/0281553 A1* | 10/2013 | Kubic | G21D 9/00 |
| | | | 518/702 |
| 2013/0306311 A1* | 11/2013 | Cooper | C10G 21/08 |
| | | | 166/267 |
| 2014/0262955 A1 | 9/2014 | Cooper et al. | |
| 2015/0047465 A1* | 2/2015 | Langley | C01B 3/348 |
| | | | 75/10.65 |
| 2015/0050344 A1* | 2/2015 | Watson | A61K 33/00 |
| | | | 424/489 |
| 2015/0108040 A1* | 4/2015 | Lord, III | B01D 19/0015 |
| | | | 208/251 R |
| 2015/0218462 A1* | 8/2015 | Lord, III | C10G 21/06 |
| | | | 208/251 R |
| 2016/0003023 A1* | 1/2016 | O'Rear | E21B 43/00 |
| | | | 166/250.01 |
| 2016/0045841 A1* | 2/2016 | Kaplan | C10G 1/02 |
| | | | 429/49 |
| 2016/0122658 A1 | 5/2016 | O'Rear et al. | |
| 2016/0332108 A1 | 11/2016 | O'Rear et al. | |
| 2018/0340174 A1* | 11/2018 | Lundorf | C12N 15/1068 |
| 2019/0275464 A1* | 9/2019 | Mazyck | B01D 53/869 |

FOREIGN PATENT DOCUMENTS

| | | |
|---|---|---|
| CN | 202533285 U | 11/2012 |
| CN | 103149057 A | 6/2013 |
| CN | 103293326 A | 9/2013 |
| CN | 105699160 A | 6/2016 |
| CN | 107389387 A | 11/2017 |
| CN | 108020601 A | 5/2018 |
| CN | 207585997 U | 7/2018 |
| JP | 2016-070726 A | 5/2016 |
| WO | WO-2016/108766 A1 | 7/2016 |

OTHER PUBLICATIONS

English-language Abstract of Deng et al., "Analysis on Mercury Forms in Oil and Gas," Oil and Gas Treating and Processing, vol. 31, No. 5, 5 pages (Oct. 2013).
English-language Abstract of Duan et al., "Experimental Study on Mercury Release and Adsorption During Coal Pyrolysis," PTCA Journal of Taiyuan University of Technology, vol. 41, No. 5, 3 pages (Sep. 2010).
English-language Abstract of Leng et al., "Discussion on Analysis Method of Trace Mercury in Liquefied Natural Gas," Guangzhou Chemical Industry, vol. 42, No. 23, 3 pages (Dec. 2014).
English-language Abstract of Li, "Determination of Mercury in Crude Oil by Cold Atomic Absorption Spectrometry," Chinese Journal of Spectroscopy Laboratory, vol. 21, No. 4, 3 pages (Jul. 2004).
English-language Abstract of Liu et al., "Advance of Research on Mercury and its Compounds Collecting and Measuring Methods," Natural Gas Geoscience, vol. 17, No. 4, 7 pages (Aug. 2006).
English-language Abstract of Tu, "Preliminary Study on Mercury Occurrence in Source Rocks," ACTA Sedimentolgica Sinica, vol. 3, No. 1, 7 pages (Jan. 1985).
English-language Abstract of Wang et al., "AFS Determination of Pb, As, and Hg in Crude Oil with Microwave Assisted Sample Digestion," PTCA (Part B: Chem. Anal.), vol. 48, No. 9, 3 pages (2012).
English-language Abstract of Wei et al., "An Introduction to XG-7Z Zeeman Mercury Measurement Instrument and the Analytical Method for Trace Concentrations of Mercury," Geophysical &Geochemical Exploration, vol. 38, No. 2, 8 pages (Apr. 2014).
English-language Abstract of Xue, "Research Progress on Analytical Methods of Mercury in Petroleum," Petroleum and Petrochemical Today, vol. 16, No. 6, 4 pages (Jun. 2008).
English-language translation of National Environmental Protection Standard of the People's Republic (HJ 543-2009): Stationary source emission-determiniation of mercury—cold atomic absorption spectrophotometry, 4 pages (Dec. 30, 2009).
English-language translation of National Standard of the People's Republic (GB/T 16157-1996): The determination of particulates and sampling methods of gaseous pollutants emitted from exhaust gas of stationary source, 4 pages (Mar. 6, 1996).
English-language translation of Paragraph 5, p. 10 of Xinliang, Zhao, "Experimental Study on the Transformation of Mercury Element During Coal Pyrolysis Gasification," Huazhong University of Science and Technology Master's Thesis, 3 pages (Jan. 2012).
Australian First Examination Report, App. No. 2019202479, PetroChina Company Limited, 6 pages (dated Nov. 20, 2019).
Australian First Examination Report, App. No. 2019202485, PetroChina Company Limited, 6 pages (dated Nov. 29, 2019).
Brahma, N., "The on line determination of mercury in process streams using atomic spectrometry," Ph.D. Thesis, University of Plymouth (Plymouth, United Kingdom), 249 pages (Nov. 2000).
Hoffart et al., "A two-step acid mercury removal process for pulverized coal," Fuel, vol. 85. pp. 1166-1173 (2006).
Lopez-Anton et al., "Analytical methods for mercury analysis in coal and coal combustion by-products," Int'l Journal of Coal Geology, 94, 47 pages (2012).
Smith, C., "Isotopic geochemistry of mercury in active and fossil hydrothermal systems," Ph.D. Thesis, University of Michigan (Ann Arbor, Michigan), 174 pages (2010).
Australian First Examination Report, App. No. 2019202470, PetroChina Company Limited, 5 pages (dated Apr. 16, 2020).

* cited by examiner

METHODS AND DEVICES FOR DETECTING MERCURY ISOTOPES IN CRUDE OIL

CROSS-REFERENCE TO RELATED PATENT APPLICATIONS

This application claims the benefit of Chinese Patent Application No. 201811284132.6, filed Oct. 31, 2018, which is incorporated herein by reference in its entirety.

TECHNICAL FIELD

The present invention relates to a field of crude oil exploitation. Particular, the present invention relates to a method and device for detecting mercury isotopes in crude oil.

BACKGROUND

As a worldwide heavy metal pollutant with severe physiological toxicity, mercury may be released by fossil fuel as the largest source for atmospheric mercury. Various studies have been reported at home and abroad on mercury in coal and its release amount from coal upon combustion as well as the environmental effects. However, there are few studies on mercury in crude oil, mainly because the crude oil is complex in composition, inflammability and explosibility, and generally has a low content of mercury therein, which causes a great uncertainty in the pretreatment or enrichment process for the mercury analysis in crude oil. Thus, there is still no effective method and device to obtain the low mercury content in crude oil. At present, the studies about mercury in crude oil mainly focus on the mercury morphological analysis and the total mercury content in commercial gasoline and its release amount. The pretreatment or enrichment process includes toluene dilution-BrCl/HCl extraction, wet extraction, microwave digestion, high temperature pyrolysis and so on. Among those, it is difficult to recover mercury from various types of crude oils for the process of the toluene dilution-BrCl/HCl extraction and wet extraction; for the process of microwave digestion, a large amount of gas may be generated, making it explosive and having less volume for sample analysis, which is only suitable for a crude oil sample with high mercury content, rather than a low-mercury-content crude oil sample having a mercury content in ppb level; and for a process of high-temperature tubular-furnace pyrolysis, it has been widely used in the mercury analysis for environmental samples, which shows advantages such as little interference by sample matrix and good mercury recovery rate in the mercury analysis for organic soil and coal, etc.

SUMMARY

An object of the present disclosure is to provide a device for detecting mercury isotopes in crude oil.

Another object of the present disclosure is to provide a method for detecting mercury isotopes in crude oil.

To achieve the above objects, in one aspect, the present disclosure provides a device for detecting mercury isotopes in crude oil, which includes an enrichment-absorption system and a secondary purification-enrichment system for mercury isotopes, wherein the enrichment-absorption system includes an air-background mercury absorption system 1, a pyrolysis/cracking system 2, and a mercury-sample absorption system 3 connected in series with pipe lines, and a vacuum pump 4, wherein the vacuum pump 4 is connected to the mercury-sample absorption system 3 through a pipe line; the secondary purification-enrichment system includes a nitrogen-gas cylinder 5, a collection bottle 9 with potassium-permanganate absorption liquid, and a secondary enrichment-absorption bottle 10 connected in series with pipe lines, wherein the secondary purification-enrichment system further includes a stannous-chloride storage bottle 7, which is connected to a pipe line between the nitrogen-gas cylinder and the collection bottle 9 with potassium-permanganate absorption liquid via a peristaltic pump 8 and through a pipe line.

In accordance with some specific embodiments, in the device, the air-background mercury absorption system 1 includes three impact samplers connected in series with pipe lines; the pyrolysis/cracking system 2 includes a pyrolysis chamber 21 and a cracking chamber 22 connected in series with pipe lines; said pyrolysis chamber 21 is connected via a pipe line to the last impact sampler in the connection order in the air-background mercury absorption system 1; the mercury-sample absorption system 3 includes five impact samplers connected in series with pipe lines, wherein the first impact sampler in the connection order is connected via a pipe line to the cracking chamber 22 of the pyrolysis/cracking system 2; the vacuum pump 4 is connected via a pipe line to the last impact sampler in the connection order of the mercury-sample absorption system 3.

In accordance with some specific embodiments, in the device, the air-background mercury absorption system 1 further comprises an air-background mercury absorption tank 14, in which the three impact samplers in the air-background mercury absorption system 1 are disposed.

In accordance with some specific embodiments, in the device, the mercury-sample absorption system 3 further comprises a mercury-sample absorption tank 16, in which the five impact samplers in the mercury-sample absorption system 3 are disposed.

In accordance with some specific embodiments, in the device, the secondary purification-enrichment system further comprises a secondary purification-enrichment tank 15, in which the collection bottle 9 with potassium-permanganate absorption liquid and the secondary enrichment-absorption bottle 10 in the secondary purification-enrichment system are disposed.

In accordance with some specific embodiments, in the device, each of the three impact samplers in the air-background mercury absorption system 1 has a volume of 500 mL.

In accordance with some specific embodiments, in the device, each of the five impact samplers in the mercury-sample absorption system 3 has a volume of 500 mL.

In accordance with some specific embodiments, in the device, all the three impact samplers in the air-background mercury absorption system 1 and the five impact samplers in the mercury-sample absorption system 3 are made of glass material.

In accordance with some specific embodiments, in the device, the pyrolysis/cracking system 2 is a dual-chamber quartz tube high-temperature pyrolysis/cracking furnace.

The dual-chamber high-temperature pyrolysis/cracking furnace with a quartz tube has an inn tube of quartz tube, and the temperature is controlled by a preset program, wherein a front chamber, which is a sample pyrolysis chamber with an inner diameter of 35 mm and a length of 100 mm, can be slowly heated in a program controlling manner to elevate the temperature from room temperature to 800° C. so that the crude oil sample can be completely pyrolyzed, while a rear chamber, which is cracking chamber at a constant temperature of 1100° C., has an inner diameter of 35 mm and a length of 300 mm.

The three impact samplers in the air-background mercury absorption system 1, in the connection order, are respectively a first impact sampler 11 containing aqua regia, a second impact sampler 12 containing aqua regia and a third impact sampler 13 containing an aqueous sodium hydroxide solution; the pyrolysis chamber 21 is connected to the third impact sampler 13 through a pipe line;

The five impact samplers in the mercury-sample absorption system 3, in the connection order, are respectively a fourth impact sampler 31 containing a stannous chloride solution, an empty fifth impact sampler 32, a sixth impact sampler 33 containing an acidic potassium permanganate solution, a seventh impact sampler 34 containing an aqueous sodium hydroxide solution and an eighth impact sampler 35 containing a silica gel, wherein the fourth impact sampler 31 is connected via a pipe line to the cracking chamber 22 in the pyrolysis/cracking system 2.

In accordance with some specific embodiments, in the device, each of the impact samplers 11, 12, 13, 31, 32, 33, 34, 35 is a borosilicate glass bottle and is provided with a gas inlet and a gas outlet at the respective top thereof, wherein the gas inlet communicates with the inner space of the bottle through a glass tube which is provided inside the bottle and extends to the lower part of the bottle.

In accordance with some specific embodiments, in the device, the aqueous sodium hydroxide solutions used in the air-background mercury absorption system 1 and the mercury-sample absorption system 3, has a concentration of 30 w/v %, the acidic potassium permanganate aqueous solution has a potassium permanganate concentration of 1 w/v %, and an acid concentration of 10 v/v %, wherein the acid is sulfuric acid.

In accordance with some specific embodiments, in the device, the aqua regia in the first impact sampler and the second impact sampler are independently used in an amount of ⅕ to ⅓ of the volume of each impact sampler.

In accordance with some specific embodiments, in the device, the aqueous sodium hydroxide solution in the air-background mercury absorption system 1 is used in an amount of ⅕ to ⅓ of the volume of the third impact sampler.

In accordance with some specific embodiments, in the device, the stannous chloride solution in mercury-sample absorption system 3 is used in an amount of ⅕ to ⅓ of the volume of the fourth impact sampler 31.

In accordance with some specific embodiments, in the device, the acidic potassium permanganate aqueous solution in the mercury-sample absorption system 3 is used an in an amount of ⅕ to ⅓ of the volume of the sixth impact sampler 33.

In accordance with some specific embodiments, in the device, the aqueous sodium hydroxide solution in the mercury-sample absorption system 3 is used in an amount of ⅕ to ⅓ of the volume of the seventh impact sampler 34.

In accordance with some specific embodiments, in the device, the collection bottle 9 with potassium permanganate absorption liquid contains a potassium permanganate absorption liquid in which mercury isotopes are absorbed, and the secondary enrichment-absorption bottle 10 contains an acidic potassium permanganate aqueous solution having a potassium permanganate concentration of 1 w/v %, and an acid concentration of 10 v/v %, wherein the acid is sulfuric acid.

In accordance with some specific embodiments, in the device, the secondary purification-enrichment system further comprises a mercury-trapping gold tube 6 which is disposed on a pipe line connecting the nitrogen-gas cylinder 5 and the collection bottle 9 with potassium permanganate absorption liquid, and approximates to the gas outlet of the nitrogen-gas cylinder 5.

In accordance with some specific embodiments, the device further comprises a detector for detecting the total mercury content of the mercury enriched in the secondary enrichment-absorption bottle 22 and a detector for detecting the composition of stable isotopes of the mercury enriched in the secondary enrichment-absorption bottle 22.

In accordance with some specific embodiments, in the device, the detector for detecting the total mercury content of the mercury enriched in the secondary enrichment-absorption bottle 22 is a cold atomic fluorescence mercury detector, and the detector for detecting the composition of stable isotopes of the mercury enriched in the secondary enrichment-absorption bottle 22 is a multi-collector inductively-coupled plasma mass spectrometer.

In accordance with some embodiments, in the device, the vacuum pump 4 is a vacuum diaphragm pump.

In another aspect, the present disclosure provides a method for detecting mercury isotopes in crude oil, wherein the method comprises the steps of:

(1) primary enrichment: heating a crude oil sample to perform pyrolysis and cracking until the crude oil sample is completely cracked, absorbing the gas released by heating the crude oil sample with an acidic potassium permanganate aqueous solution to enrich the mercury element in the crude oil sample, and collecting all of the acidic potassium permanganate solution in which the mercury element is enriched in step (1);

(2) mercury purification and enrichment: reducing the mercury absorbed in the step (1) to mercury vapor with a stannous chloride solution, and then purifying and enriching the mercury vapor by using an acidic potassium permanganate aqueous solution;

(3) detecting the acidic potassium permanganate solution in which the mercury vapor is enriched in step (2) to determine the total mercury content therein;

(4) detecting the acidic potassium permanganate solution in which the mercury vapor is enriched in step (2) to determine the composition/content of stable mercury isotopes therein.

In accordance with some specific embodiments, in the method, the step (1) comprises heating the crude oil sample to the boiling point of the light hydrocarbon and holding the temperature until the light hydrocarbon volatilizes completely, and then gradiently increasing the temperature at an interval of 80 to 120° C., with each temperature gradient maintained for 20 to 40 minutes until the crude oil sample becomes a solid residue, after that subjecting the solid residue to further cracking by increasing the temperature until the cracking is complete.

In accordance with some specific embodiments, in the method, step (1) comprises weighing the crude oil sample in a specially prepared quartz-based sample boat (23), slowly increasing the temperature to 450° C. and holding the temperature so that the crude oil sample is slightly boiled to slowly volatilize light hydrocarbon components; after the crude oil sample stops boiling (via visual observation), increasing the temperature at a temperature interval (generally 100° C.) and holding for 30 minutes until the temperature reaches to 750° C., holding the temperature until the sample becomes a solid residue; when the solid residue has no gaseous fraction, continuing to increasing the temperature to 1000° C. and holding the temperature for 15 minutes so that the crude oil fraction is slowly volatilized; after it is completely cracked at 1100° C., absorbing the mercury absorbed and released by the mercury pre-enrichment system with a solution of 1% $KMnO_4$-10% $H_2SO_4$.

In accordance with some specific embodiments, in the method, step (1) further comprises absorbing the gas product released by heating the crude oil sample sequentially with a stannous chloride solution and an acidic potassium permanganate solution, and passing the residual gas product after the absorption into a container containing a silica gel.

In accordance with some specific embodiments, in the method, the acidic potassium permanganate aqueous solution in step (1) has a potassium permanganate concentration of 1 w/v %, and an acid concentration of 10 v/v %, wherein the acid is sulfuric acid.

In accordance with some specific embodiments, in the method, each of the stannous chloride solutions in step (1) and step (2) independently has a concentration of 15 to 25 w/v %.

In accordance with some specific embodiments, in the method, step (2) comprises pumping a stannous chloride solution into the acidic potassium permanganate solution in which a crude oil is absorbed, collected in step (1), using nitrogen gas as a carry gas, to reduce mercury to mercury vapor, and feeding the mercury vapor into the acidic potassium permanganate aqueous solution with nitrogen gas to purify and enrich the mercury vapor.

In accordance with some specific embodiments, in the method, the nitrogen gas used as a carry gas in step (2) is subjected to mercury trapping treatment prior to contacting the acidic potassium permanganate solution collected in step (1).

In accordance with some specific embodiments, in the method, step (3) is the step of detecting the acidic potassium permanganate solution in which the mercury vapor is enriched in step (2) with a cold atomic fluorescence mercury detector; and step (4) is the step of detecting the acidic potassium permanganate solution in which the mercury vapor is enriched in step (2) with a multi-collector inductively coupled plasma mass spectrometer.

In accordance with some specific embodiments, in the method, step (3) is the step of detecting the acidic potassium permanganate solution in which the mercury vapor is enriched in step (2) with a cold atomic fluorescence Brooks model III mercury detector; and step (4) is the step of detecting the acidic potassium permanganate solution in which the mercury vapor is enriched in step (2) with a Nu plasma type multi-collector inductively coupled plasma mass spectrometer.

A cold atomic fluorescence Brooks model III mercury detector is used to analyze the total mercury content in the sample after secondary purification and enrichment. Since the mercury content in crude oil is generally low, in order to ensure the accuracy of sample analysis, the main reagent for mercury pre-enrichment and absorption must be a chemical reagent with low mercury blank.

In accordance with some specific embodiment, the method further comprises a step (5) of: comparing and analyzing the composition information for the mercury isotopes in mass fractionation and mass-independent fractionation in different types of crude oils based on the detection results in steps (3) and (4), establishing the mercury information characteristics in mass fractionation and mass-independent fractionation in different types of crude oils, and establishing an identification parameter system for crude oil genesis and evaluating the favorable exploration area.

In accordance with some specific embodiments, the method comprises performing a detection using the device for detecting mercury isotopes according to any one in the present invention in crude oil.

In accordance with some specific embodiments, in the method, step (1) comprises weighing a crude oil sample in a specially-made quartz sample boat and placing it at the front end in the pyrolysis chamber 21, followed by quickly connecting, and starting the power supply for the tube furnace and the vacuum diaphragm pump to heat the pyrolysis chamber 21 slowly to 450° C. and holding the temperature so that the crude oil sample is slightly boiled to slowly volatilize light hydrocarbon components; after the crude oil sample stops boiling (via visual observation), increasing the temperature at a temperature interval (generally 100° C.) and holding the temperature for 30 minutes until the temperature reaches to 750° C., holding the temperature until the sample becomes a solid residue, thereafter pushing the sample boat to the middle of the pyrolysis chamber 21; when the solid residue has no gaseous fraction, continue to increase the temperature to 1000° C. and holding the temperature for 15 minutes so that the crude oil fraction is slowly volatilized; after it is completely cracked at 1100° C. via the cracking chamber 22, absorbing the mercury absorbed and released by the mercury pre-enrichment system with a solution of 1% $KMnO_4$-10% $H_2SO_4$.

Due to the different compositions and volatilities (when heated) of the crude oils depending on the types of crude oils, the program settings for the pyrolysis temperature and holding time in the pyrolysis chamber 21 can also be adjusted according to the properties of the crude oils, mainly provided that the crude oil can be prevented from producing black smokes by flaming so as to affect the enrichment of mercury by acidic potassium permanganate solution for absorption. Typically, a crude oil sample having a mercury content in ppb levels requires 7 to 8 hours for the pyrolysis/cracking pre-concentration procedure. If the crude oil sample has a low mercury content, its amount for the pyrolysis/cracking pre-enrichment can be increased.

In accordance with some specific embodiments, in the method, all glassware in step (1) are washed with 15% $HNO_3$ solution and ultrapure water before each use. Prior to sample pre-enrichment, the cracking chamber 22 needs to be heated to 1100° C. and be held until the end of the experiment. The air-background mercury absorption system and the mercury-sample absorption system are installed, the corresponding solution or reagent is added into the impact samplers, and connected to the quartz inner tube in the tube furnace, and finally the vacuum pump is connected. The air tightness of the system is checked by connecting cumulative flow meters in front of the air-background mercury absorption system and in front of the vacuum diaphragm pump, respectively, before starting the experiment.

After the above process is completed, the air-background mercury absorption system 1, the pyrolysis/cracking system 2, the mercury-sample absorption system 3, the vacuum pump 4 and the power source are sequentially disconnected in this order, and the acidic potassium permanganate absorption solution is quickly recovered in a 150 mL borosilicate glass bottle, sealed, designated as pre-enriched sample, and thus the pre-enrichment process is complete.

In accordance with some specific embodiments, in the method, the crude oil in step (1) is originated from a crude oil sample of a normally producing well in an oilfield, and the types of crude oils include crude oils of different genetic types and different regions, and crude oils of different natures, such as bitumen, heavy crude oil, thick oil, medium oil and normal oil, etc.

In accordance with some specific embodiments, in the method, the detection of the mercury content in step (3) is carried out by using a cold atomic fluorescence Brooks model III mercury detector to analyze the total mercury content in a secondary enriched sample. Before each instrument analysis, it is necessary to perform blank detection on the mercury-trapping gold tube and purging-and-capturing system, and draw a standard curve after the instrument noise drops and the baseline is stable. The standard curve is required to have $R^2$ of larger than 0.99. Each sample is analyzed twice. Blank analysis is carried out for every 10 samples.

In accordance with some specific embodiments, in the method, the mercury isotope composition in mass fractionation and mass-independent fractionation in step (3) is carried out by an analytical instrument, Nu plasma type multi-collector inductively coupled plasma mass spectrometer manufactured by Nu Instruments, UK, which is a dual-focus magnetic mass spectrometer. In the instrument, a continuous-flow feeding system is used, and the sample is reduced by a $SnCl_2$ solution to produce $Hg^0$ gas which is introduced into a plasma source, and the mass discrimination correction of the instrument is done with Tl ions produced by an Apex-Q atomizer (CETAC Technologies, Omaha, USA). The entire feeding process is performed by a compact peristaltic pump (Gilson Corp., USA) at a feeding flow rate of 0.75 ml/min. The receiving system of the instrument has 12 fixed Faraday cups and 3 ion receivers. Among those, seven Faraday Cups are used for Hg Isotopes detection. Ar gas with high purity is used as carrier gases for feeding and plasma in the experiment. In order to ensure the accuracy of mercury isotope detection, the mercury concentration in the sample shall be maintained between 0.5 to 2 µg/l. The isotope composition is expressed in 1000 lnα with respect to the standard (NIST SRM 3133).

In accordance with some specific embodiments, in the method, the information for different types of crude oil is compared and analyzed in step (4), and the value range and the critical parameters regarding the mercury isotope ratio are established by analyzing the mercury isotopes in crude oils from different deposit environment sources, so that the mercury information characteristics for the mass fractionation and mass-independent fractionation in different types of crude oil are summarized. The source of oil and gas can be determined by rapid mercury isotope analysis using the crude oil obtained from a newly drilled well, so as to guide exploration deployment.

In summary, the present disclosure provides a method for detecting mercury isotopes in crude oils and a device therefor. The method according to the present disclosure has following advantages:

The mercury enrichment system for the mercury analysis in crude oils of the present disclosure, which comprises quartz-tube double-chamber high-temperature pyrolysis/cracking and acid potassium permanganate absorption, leads to relatively complete release of mercury in a crude oil sample, and eliminate interference and influence of other substances in the crude oil on mercury analysis; and the value range and critical value parameters for mercury isotope ratios in different types of crude oils are found by comparing and analyzing the mercury isotope composition information of mass fractionation and mass-independent fractionation in different types of crude oils, so that a new method for oil source comparison may be established.

DETAILED DESCRIPTION

In the following, a detailed description is provided for the implementation and beneficial effects of the present disclosure by way of specific examples, which are intended to help a better understanding for the essence and features of the present disclosure and are not intended to limit the implementable scope of the present disclosure.

Example 1

Figure 1:
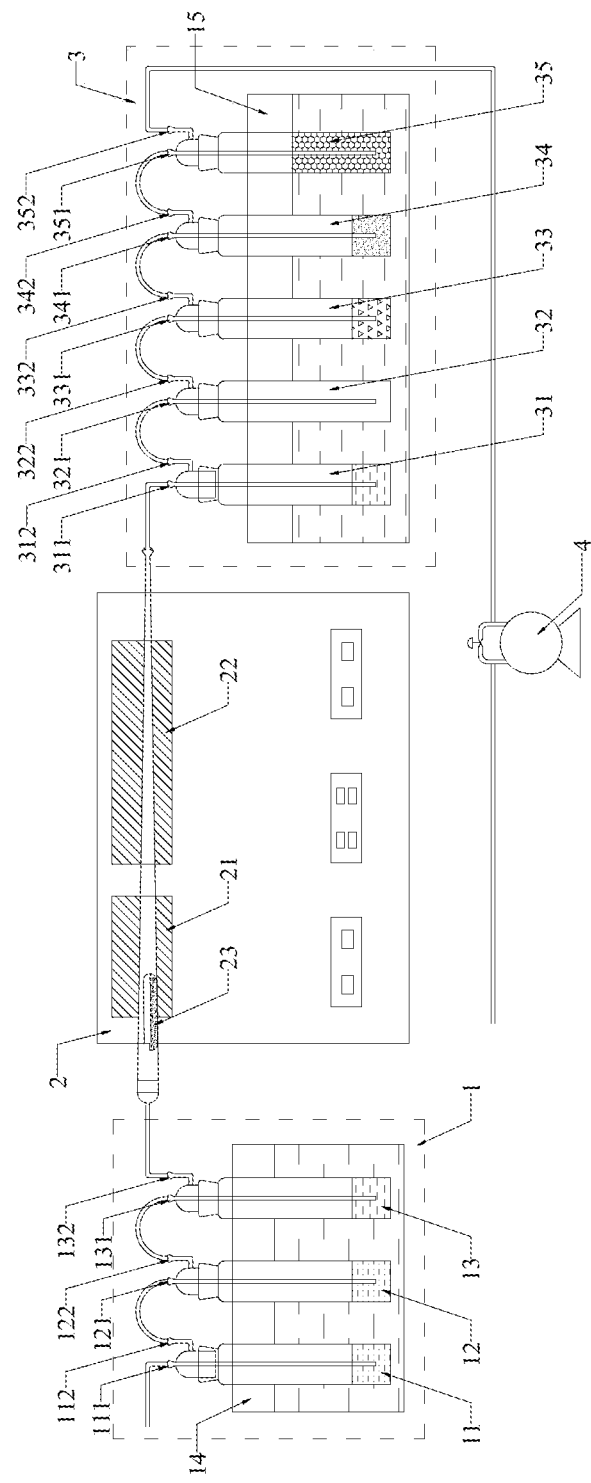
FIG. 1 is a schematic diagram of an enrichment-absorption system in Example 1.
Figure 2:
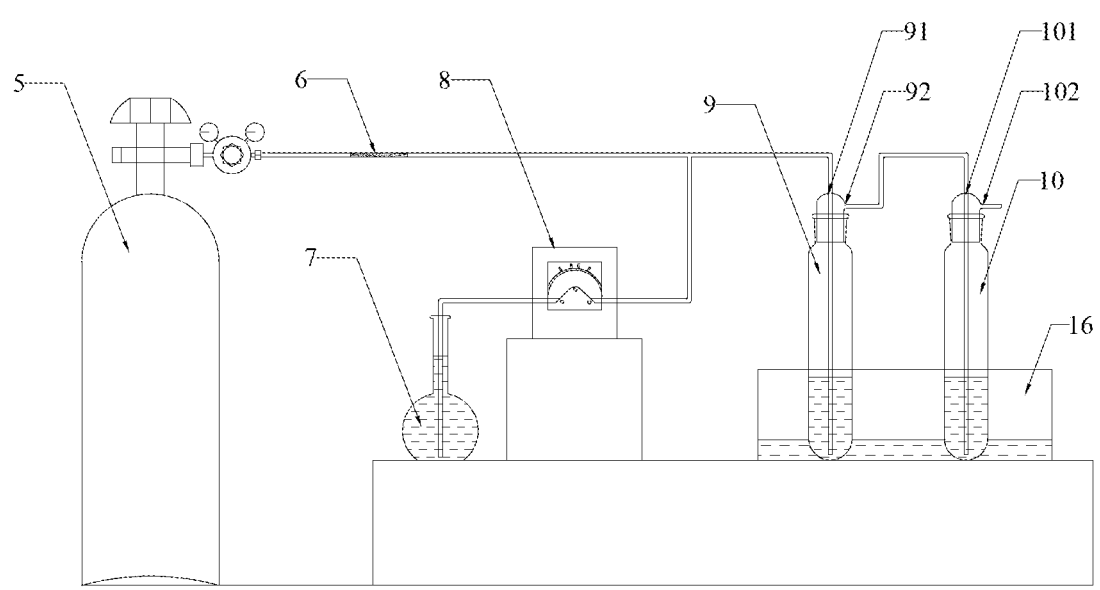
FIG. 2 is a schematic diagram of the secondary purification-enrichment system in Example 1.

A device for detecting mercury isotopes in crude oils, comprising an enrichment-absorption system for mercury isotopes as shown in FIG. 1 and a secondary purification-enrichment system as shown in FIG. 2, wherein the enrichment-absorption system comprises an air-background mercury absorption system 1, a pyrolysis/cracking system 2, and a mercury-sample absorption system 3 connected in series with pipe lines, and a vacuum diaphragm pump 4 which is connected to the mercury-sample absorption system 3 through a pipe line; and a Brooks model III cold atomic fluorescence mercury detector (not shown) for detecting the total mercury content of the mercury enriched in the secondary enrichment-absorption bottle 22 and a Nu plasma type multi-collector inductively coupled plasma mass spectrometer (not shown) manufactured by Nu Instruments, UK for detecting the composition of stable isotopes of the mercury enriched in the secondary enrichment-absorption bottle 22;

The air-background mercury absorption system 1 comprises a first impact sampler 11 containing aqua regia, a second impact sampler 12 containing aqua regia and a third impact sampler 13 containing an aqueous sodium hydroxide solution (30 w/v %) connected in series with pipe lines; each of the impact samplers is a borosilicate glass bottle with a volume of 500 ml, and is provided with a gas inlet and a gas outlet at the respective top thereof, wherein the gas inlet communicates with the inner space of the bottle through a glass tube which is provided inside the bottle and extends to the lower part of the bottle; the air-background mercury absorption system 1 further includes an air-background mercury absorption tank 14 in which the first impact sampler 11, the second impact sampler 12, and the third impact sampler 13 are disposed.

The pyrolysis/cracking system 2 comprises a pyrolysis chamber 21 (having an inner diameter of 35 mm and a length of 100 mm) and a cracking chamber 22 (having an inner diameter of 35 mm and a length of 300 mm) connected in series with pipe lines; said pyrolysis chamber 21 is connected via a pipe line to the last impact sampler in the connection order in the air-background mercury absorption system 1; and the pyrolysis chamber 21 is connected to the third impact sampler 13 through a pipe line;

The mercury-sample absorption system 3 comprises a fourth impact sampler 31 containing a stannous chloride solution, an empty fifth impact sampler 32, a sixth impact sampler 33 containing an acidic potassium permanganate solution (having a potassium permanganate concentration of 1 w/v %, and an acid concentration of 10 v/v %, wherein the acid is sulfuric acid), a seventh impact sampler 34 containing an aqueous sodium hydroxide solution (30 w/v %) and an eighth impact sampler 35 containing a silica gel, which are connected in series with pipe lines; each of the impact samplers is a borosilicate glass bottle with a volume of 500 ml, and is provided with a gas inlet and a gas outlet at the respective top thereof, wherein the gas inlet communicates with the inner space of the bottle through a glass tube which is provided inside the bottle and extends to the lower part of the bottle; the fourth impact sampler 31 is connected to the cracking chamber 22 in the pyrolysis/cracking system 2 through a pipe line; the first impact sampler in the connection order is connected via a pipe line to the cracking chamber 22 in the pyrolysis/cracking system 2; the vacuum pump 4 is connected via a pipe line to the last impact sampler in the connection order in the mercury-sample absorption system 3. The mercury-sample absorption system 3 further includes a mercury-sample absorption tank 16, in which the fourth impact sampler 31, the fifth impact sampler 32, the sixth impact sampler 33, the seventh impact sampler 34, and the eighth impact sampler 35 are disposed.

The secondary purification-enrichment system comprises a nitrogen gas cylinder 5, a mercury-trapping gold tube 6, a collection bottle 9 with potassium-permanganate absorption liquid containing a potassium permanganate absorption liquid in which mercury isotopes is absorbed, and a secondary enrichment-absorption bottle 10 containing an acidic potassium permanganate aqueous solution (having a potassium permanganate concentration of 1 w/v %, and an acid concentration of 10 v/v %, wherein the acid is sulfuric acid) connected in series with pipe lines, and the secondary purification-enrichment system further comprises a stannous-chloride storage bottle 7, which is connected to a pipe line between the nitrogen-gas cylinder and the collection bottle 9 with potassium-permanganate absorption liquid via a peristaltic pump 8 and through a pipe line. The secondary purification-enrichment system further comprises a secondary purification-enrichment tank 15, in which the collection bottle 9 with potassium-permanganate absorption liquid and the secondary enrichment-absorption bottle 10 are disposed.

Using the device described above, a method for detecting mercury isotopes is carried out, comprising the steps of:

(1) primary enrichment: weighing a crude oil sample in a specially prepared quartz-based sample boat 23, heating the crude oil sample to 450° C. and holding the temperature to completely volatilize light hydrocarbon components; after that, gradually increasing the temperature at a temperature interval of 100° C., with each temperature gradient maintained for 30 minutes until the crude oil sample becomes a solid residue; then heating the solid residue to 750° C., holding the temperature until the sample becomes a solid residue; when the solid residue has no gaseous fraction, continuing to increase the temperature to 1000° C. and holding the temperature for 15 minutes so that the crude oil fraction is slowly volatilized; after it is completely cracked at 1100° C., absorbing the mercury absorbed and released by the mercury pre-enrichment system sequentially with a stannous chloride solution (20 w/v %) and a solution of a solution of 1% KMnO$_4$-10% H$_2$SO$_4$, and then collecting all of the acidic potassium permanganate solution in which mercury elements are enriched in the step (1);

(2) mercury purification and enrichment: pumping a stannous chloride solution (20 w/v %) into the acidic potassium permanganate solution in which a crude oil is absorbed, collected in step (1), using nitrogen gas subjected to mercury trapping treatment as a carry gas to reduce mercury to mercury vapor, and feeding the mercury vapor into the acidic potassium permanganate aqueous solution with nitrogen gas to purify and enrich the mercury vapor;

(3) detecting the acidic potassium permanganate solution in which the mercury vapor is enriched in step (2) with a cold atomic fluorescence Brooks model III mercury detector to determine the total mercury content therein;

(4) detecting the acidic potassium permanganate solution in which the mercury vapor is enriched in step (2) with a Nu plasma type multi-collector inductively coupled plasma mass spectrometer to determine the composition of stable mercury isotopes therein.

(5) comparing and analyzing the composition information for the mercury isotopes in mass fractionation and mass-independent fractionation in different types of crude oils based on the detection results in steps (3) and (4), establishing the mercury information characteristics in mass fractionation and mass-independent fractionation in different types of crude oils, and establishing an identification parameter system for crude oil genesis and evaluating the favorable exploration area. The results are as follows:

The crude oil produced by the lower tertiary lacustrine source rocks under the typical Bohai Bay Basin and the crude oil produced by the Ordovician marine source rocks in the Tarim Basin were collected and analyzed for mercury isotopes, respectively. The results are as follows.

Continental crude oil in Bohai Bay Basin:

Well No. NP101: $\delta^{202}$Hg value: −1.85‰±0.16‰, $\Delta^{199}$Hg value: 0.09‰±0.06‰;

Well No. LPN1: $\delta^{202}$Hg value: −2.01‰±0.06‰, $\Delta^{199}$Hg value: 0.14‰±0.07‰;

Well No. N11-2: $\delta^{202}$Hg value: −1.96‰±0.23‰, $\Delta^{199}$Hg value: 0.11‰±0.04‰;

Marine crude oil in Tarim Basin:

Well No. FY101: $\delta^{202}$Hg value: −0.17‰±0.12‰, $\Delta^{199}$Hg value: 0.21‰±0.08‰;

Well No. ZG83: $\delta^{202}$Hg value: 0.09‰±0.32‰, $\Delta^{199}$Hg value: 0.29‰±0.05‰;

Well No. H701: $\delta^{202}$Hg value: 0.21‰±0.09‰, $\Delta^{199}$Hg value: 0.26‰±0.09‰;

The analysis results are in good agreement with the crude genesis. Therefore, α$\delta^{202}$Hg value of −1‰ and $\Delta^{199}$Hg value of 0.2‰ for the crude oils may be used as indices to distinguish continental oils and marine oils. If the value is respectively larger than the index, the crude oil is a marine oil, conversely, it is a continental oil.

What is claimed is:

1. A device for detecting mercury isotopes in crude oil, which comprises an enrichment-absorption system and a secondary purification-enrichment system for mercury isotopes, wherein the enrichment-absorption system comprises an air-background mercury absorption system, a pyrolysis/cracking system, and a mercury-sample absorption system connected in series with pipe lines, and a vacuum pump, wherein the vacuum pump is connected to the mercury-sample absorption system through a pipe line; and the secondary purification-enrichment system comprises a nitrogen-gas cylinder, a collection bottle with potassium-permanganate absorption liquid, and a secondary enrichment-absorption bottle connected in series with pipe lines, wherein the secondary purification-enrichment system further comprises a stannous-chloride storage bottle, which is connected to a pipe line between the nitrogen-gas cylinder and the collection bottle with potassium-permanganate absorption liquid via a peristaltic pump and through a pipe line.

2. The device according to claim 1, wherein the air-background mercury absorption system comprises three impact samplers connected in series with pipe lines;
the pyrolysis/cracking system comprises a pyrolysis chamber and a cracking chamber connected in series with pipe lines, wherein the pyrolysis chamber is connected via a pipe line to the last impact sampler in the connection order in the air-background mercury absorption system; and
the mercury-sample absorption system comprises five impact samplers connected in series with pipe lines, wherein the first impact sampler in the connection order is connected via a pipe line to the cracking chamber of the pyrolysis/cracking system, and the vacuum pump is connected via a pipe line to the last impact sampler in the connection order of the mercury-sample absorption system.

3. The device according to claim 2, wherein the three impact samplers in the air-background mercury absorption system, in the connection order, are respectively a first impact sampler containing aqua regia, a second impact sampler containing aqua regia and a third impact sampler containing an aqueous sodium hydroxide solution, and the pyrolysis chamber is connected to the third impact sampler through a pipe line; and
the five impact samplers in the mercury-sample absorption system, in the connection order, are respectively a fourth impact sampler containing a stannous chloride solution, an empty fifth impact sampler, a sixth impact sampler containing an acidic potassium permanganate solution, a seventh impact sampler containing an aqueous sodium hydroxide solution and an eighth impact sampler containing a silica gel, wherein the fourth impact sampler is connected via a pipe line to the cracking chamber in the pyrolysis/cracking system.

4. The device according to claim 3, wherein each of the impact samplers is a borosilicate glass bottle and is provided with a gas inlet and a gas outlet at the respective top thereof, wherein the gas inlet communicates with the inner space of the bottle through a glass tube which is provided inside the bottle and extends to the lower part of the bottle.

5. The device according to claim 3, wherein the aqueous sodium hydroxide solutions used in the air-background mercury absorption system and the mercury-sample absorption system has a concentration of 30 w/v %, and the acidic potassium permanganate aqueous solution has a potassium permanganate concentration of 1 w/v %, and an acid concentration of 10 v/v %, the acid is sulfuric acid.

6. The device according to claim 1, wherein the collection bottle with potassium permanganate absorption liquid contains a potassium permanganate absorption liquid in which mercury isotopes are absorbed, and the secondary enrichment-absorption bottle contains an acidic potassium permanganate aqueous solution, the acidic potassium permanganate aqueous solution has a potassium permanganate concentration of 1 w/v %, and an acid concentration of 10 v/v %, the acid is sulfuric acid.

7. The device according to claim 1, wherein the secondary purification-enrichment system further comprises a mercury-trapping gold tube which is disposed on a pipe line connecting the nitrogen-gas cylinder and the collection bottle with potassium permanganate absorption liquid, and approximates to the gas outlet of the nitrogen-gas cylinder.

8. The device according to claim 1, wherein the device further comprises a detector for detecting the total mercury content of the mercury enriched in the secondary enrichment-absorption bottle and a detector for detecting the composition of stable isotopes of the mercury enriched in the secondary enrichment-absorption bottle.

9. The device according to claim 8, wherein the detector for detecting the total mercury content of the mercury enriched in the secondary enrichment-absorption bottle is a cold atomic fluorescence mercury detector, and the detector for detecting the composition of stable isotopes of the mercury enriched in the secondary enrichment-absorption bottle is a multi-collector inductively-coupled plasma mass spectrometer.

10. A method for detecting mercury isotopes in crude oil, wherein the method comprises the steps of:
(1) primary enrichment: heating a crude oil sample to perform pyrolysis and cracking until the crude oil sample is completely cracked, absorbing the gas released by heating the crude oil sample with an acidic potassium permanganate aqueous solution to enrich the mercury element in the crude oil sample, and collecting all of the acidic potassium permanganate solution in which the mercury element is enriched in step (1);
(2) mercury purification and enrichment: reducing the mercury absorbed in the step (1) to mercury vapor with a stannous chloride solution, and then purifying and enriching the mercury vapor by using an acidic potassium permanganate aqueous solution;
(3) detecting the acidic potassium permanganate solution in which the mercury vapor is enriched in step (2) to determine the total mercury content therein;
(4) detecting the acidic potassium permanganate solution in which the mercury vapor is enriched in step (2) to determine the composition/content of stable mercury isotopes therein.

11. The method according to claim 10, wherein the step (1) comprises heating the crude oil sample to the boiling point of the light hydrocarbon and holding the temperature until the light hydrocarbon volatilizes completely, and then gradiently increasing the temperature at an interval of 80 to 120° C., with each temperature gradient maintained for 20 to 40 minutes until the crude oil sample becomes a solid residue, after that subjecting the solid residue to further cracking by increasing the temperature until the cracking is complete.

12. The method according to claim 10, wherein step (1) further comprises absorbing the gas product released by heating the crude oil sample sequentially with a stannous chloride solution and an acidic potassium permanganate solution, and passing the residual gas product after the absorption into a container containing a silica gel.

13. The method according to claim 10, wherein the acidic potassium permanganate aqueous solution in step (1) has a potassium permanganate concentration of 1 w/v %, and an acid concentration of 10 v/v %, wherein the acid is sulfuric acid.

14. The method according to claim 10, wherein each of the stannous chloride solutions in step (1) and step (2) independently has a concentration of 15 to 25 w/v %.

15. The method according to claim 10, wherein step (2) comprises pumping a stannous chloride solution into the acidic potassium permanganate solution in which a crude oil is absorbed, collected in step (1), using nitrogen gas as a carry gas, to reduce mercury to mercury vapor, and feeding the mercury vapor into the acidic potassium permanganate aqueous solution with nitrogen gas to purify and enrich the mercury vapor.

16. The method according to claim 15, wherein the nitrogen gas used as a carry gas in step (2) is subjected to mercury trapping treatment prior to contacting the acidic potassium permanganate solution collected in step (1).

17. The method according to claim 10, wherein step (3) is the step of detecting the acidic potassium permanganate solution in which the mercury vapor is enriched in step (2) with a cold atomic fluorescence mercury detector; and step (4) is the step of detecting the acidic potassium permanganate solution in which the mercury vapor is enriched in step (2) with a multi-collector inductively coupled plasma mass spectrometer.

18. The method according to claim 10, wherein the method further comprises a step (5) of: comparing and analyzing the composition information for the mercury isotopes in mass fractionation and mass-independent fractionation in different types of crude oils based on the detection results in steps (3) and (4), establishing the mercury information characteristics in mass fractionation and mass-independent fractionation in different types of crude oils, and establishing an identification parameter system for crude oil genesis and evaluating the favorable exploration area.

19. The method according to claim 10, wherein the method comprises performing a detection using a device for detecting mercury isotopes in the crude oil comprising:
- an enrichment-absorption system and a secondary purification-enrichment system for mercury isotopes, wherein the enrichment-absorption system comprises an air-background mercury absorption system, a pyrolysis/cracking system, and a mercury-sample absorption system connected in series with pipe lines, and a vacuum pump, wherein the vacuum pump is connected to the mercury-sample absorption system through a pipe line; and
- wherein the secondary purification-enrichment system comprises a nitrogen-gas cylinder, a collection bottle with potassium-permanganate absorption liquid, and a secondary enrichment-absorption bottle connected in series with pipe lines, wherein the secondary purification-enrichment system further comprises a stannous-chloride storage bottle, which is connected to a pipe line between the nitrogen-gas cylinder and the collection bottle with potassium-permanganate absorption liquid via a peristaltic pump and through a pipe line.

* * * * *